(12) United States Patent
Nelms

(10) Patent No.: US 8,130,905 B1
(45) Date of Patent: Mar. 6, 2012

(54) DOSIMETRY SYSTEM AND METHOD FOR RADIATION THERAPY

(75) Inventor: Benjamin E. Nelms, Merrimac, WI (US)

(73) Assignee: Sun Nuclear Corporation, Melbourne, FL (US)

( * ) Notice: Subject to any disclaimer, the term of this patent is extended or adjusted under 35 U.S.C. 154(b) by 704 days.

(21) Appl. No.: 12/274,823

(22) Filed: Nov. 20, 2008

Related U.S. Application Data

(60) Provisional application No. 60/989,586, filed on Nov. 21, 2007.

(51) Int. Cl.
*A61N 5/10* (2006.01)

(52) U.S. Cl. .......................... 378/65; 382/131

(58) Field of Classification Search .......... 382/128–132; 378/63–65, 196
See application file for complete search history.

(56) References Cited

U.S. PATENT DOCUMENTS

| | | | |
|---|---|---|---|
| 4,450,440 A | 5/1984 | White | |
| 5,394,452 A * | 2/1995 | Swerdloff et al. | 378/65 |
| 6,038,283 A | 3/2000 | Carol et al. | |
| 6,125,335 A | 9/2000 | Simon et al. | |
| 6,175,761 B1 | 1/2001 | Frandsen et al. | |
| 6,345,114 B1 | 2/2002 | Mackie et al. | |
| 6,516,046 B1 | 2/2003 | Frohlich et al. | |
| 6,552,347 B1 | 4/2003 | Dimcovski | |
| 6,626,569 B2 | 9/2003 | Reinstein et al. | |
| 6,636,622 B2 | 10/2003 | Mackie et al. | |
| 6,810,107 B2 | 10/2004 | Steinberg | |
| 6,810,108 B2 | 10/2004 | Clark et al. | |
| 6,839,404 B2 | 1/2005 | Clark et al. | |
| 6,842,502 B2 * | 1/2005 | Jaffray et al. | 378/65 |
| 6,853,702 B2 | 2/2005 | Renner | |
| 6,888,919 B2 | 5/2005 | Graf | |
| 6,904,125 B2 | 6/2005 | Van Dyke et al. | |
| 7,076,023 B2 | 7/2006 | Ghelmansarai et al. | |
| 7,127,030 B2 | 10/2006 | Tamegai | |
| 7,221,733 B1 | 5/2007 | Takai et al. | |
| 7,233,688 B2 | 6/2007 | Ritt et al. | |
| 7,298,820 B2 | 11/2007 | Nelson | |
| 7,471,765 B2 * | 12/2008 | Jaffray et al. | 378/65 |
| 7,832,928 B2 * | 11/2010 | Topfer et al. | 378/207 |
| 2004/0068182 A1 | 4/2004 | Misra | |
| 2006/0266951 A1 | 11/2006 | Fritsch et al. | |
| 2007/0041497 A1 | 2/2007 | Schnarr et al. | |
| 2007/0071169 A1 | 3/2007 | Yeo et al. | |
| 2007/0081629 A1 | 4/2007 | Yin et al. | |
| 2008/0049896 A1 | 2/2008 | Kuduvalli | |
| 2008/0103834 A1 | 5/2008 | Reiner | |
| 2008/0107229 A1 * | 5/2008 | Thomas et al. | 378/4 |
| 2010/0020933 A1 * | 1/2010 | Topfer et al. | 378/98.11 |
| 2011/0228906 A1 * | 9/2011 | Jaffray et al. | 378/65 |

* cited by examiner

*Primary Examiner* — Nathan Ha

(74) *Attorney, Agent, or Firm* — Allen, Dyer, Doppelt Milbrath & Gilchrist, P.A.

(57) ABSTRACT

Electronic portal imaging device (EPID) images are converted to an absolute dose at a simulated absolute dose plane in a measurement phantom for supporting intensity modulated radio therapy (IMRT) dose quality assurance (QA) by geometrically projecting the EPID image as may be needed, generating an output factor correction map specific to a radiation treatment beam, multiplying an EPID image by the output factor correction map for generating an output corrected EPID image, and convolving the output corrected EPID image with a redistribution kernel for generating a relative dose at a preselected dose plane. A wide field calibration map is then applied to the relative dose for generating an absolute dose at the preselected dose plane location.

23 Claims, 12 Drawing Sheets

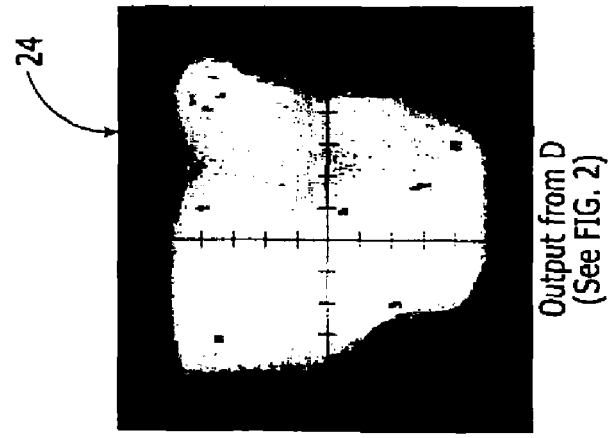
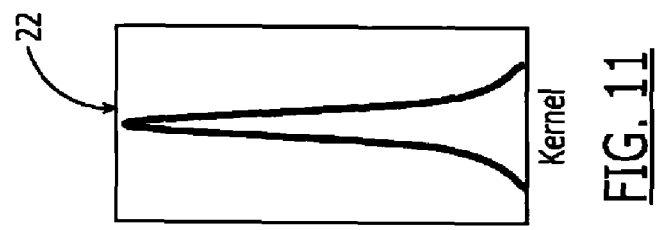
FIG. 11
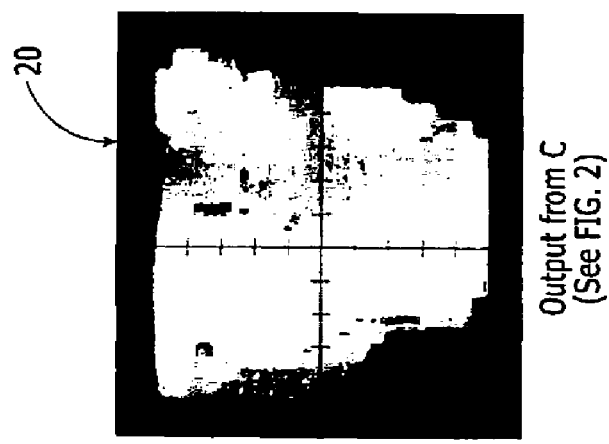

DOSIMETRY SYSTEM AND METHOD FOR RADIATION THERAPY

CROSS-REFERENCE TO RELATED APPLICATION

This application claims the benefit of U.S. Provisional Application No. 60/989,586 for "EPID Dosimetry System and Method" having filing date Nov. 21, 2007, the disclosure of which is incorporated herein by reference in its entirety, all being commonly owned.

FIELD OF INVENTION

The invention generally relates to radiation therapy equipment and radiation treatment, and in particular to systems and methods for converting electronic portal imaging device (EPID) images to simulated absolute dose planes in a measurement phantom for supporting intensity modulated radio therapy (IMRT) dose quality assurance (QA).

BACKGROUND

There is a need for an accurate estimation of absolute dose within planes, by way of example in a phantom, based on an input of Mega-voltage (MV) EPID images. As described in U.S. Pat. Nos. 6,345,114 for Method and Apparatus for Calibration of Radiation Therapy Equipment and Verification of Radiation Therapy, and 6,839,404 for System and Method for Positioning an Electric Portal Imaging Device, EPIDs is well known. Advantages of the EPID include 'online convenience, data resolution (small pixels), and data density. However, MV EPIDs are not dosimeters, as the interactions of photons leading to an EPID image are notably different than the interactions in water or tissue that lead to radiation dose. It is desirable to maintain the industry standard of measured dose-to-calculated dose to perform IMRT QA analysis. Therefore comparison of anything other than dose, such as comparing a measured image to a predicted image is an undesirable shift from comparing a measured dose plane to a calculated dose plane. Additionally, percent differences, distance to agreement (DTA), and gamma criteria used in IMRT QA are based on a dose-in-tissue/water rationale.

There is also a need for an independent and reliably robust analysis. Any QA solution that is built into a radiation delivery system is a "self check," which results in a fundamental conflict of interest due to the lack of a 3rd party independence. By way of example, exposing potential errors via independent and rigorous QA is a high ranking goal of medical physics. Relying completely on one system for planning, delivery, and QA reduces the likelihood of catching errors due to shared components, internal biases, and conflicting objectives.

Typical EPID images have pixel values that do not have dose equivalent units, for example are not centi-Gray (cGy). As a result using raw EPID images generates comparisons that are quantitative but not dosimetric. In such a case, use of standard intensity modulated radiography quality assurance (IMRT QA) analysis tools (DTA and gamma especially) is questionable unless acceptance criteria are re-established for non-dosimetric images. Additionally, the EPID image is typically acquired in a different geometry than is typical for IMRT QA. In other words, it is acquired at a different source-to-detector distance and with different build-up characteristics.

By way of further example, EPID detectors exhibit a different response with respect to energy spectra and scatter radiation than do dosimeters providing dose in tissue/water. Further, EPID images have a point spread response that is different than a dose kernel superposition of dose at depth in tissue/water. Yet further, EPID images exhibit off-axis/wide field variations in response.

There is a need for EPID-to-Dose conversions that allow IMRT QA to remain dose-based. There is also a need to estimate an absolute dose delivered in standard IMRT QA conditions including factors such as tissue equivalent buildup, source-to-detector distance, dose to tissue, and the like.

SUMMARY

The present invention provides a system and method for converting electronic portal imaging device (EPID) images to an absolute dose at a simulated absolute dose plane in a measurement phantom for supporting intensity modulated radio therapy (IMRT) dose quality assurance (QA) by projecting the EPID image geometrically as may be required, generating an output factor correction map specific to a radiation treatment beam, multiplying an EPID image by the output factor correction map for generating an output corrected EPID image, and convolving the output corrected EPID image with a redistribution kernel for generating a relative dose at a preselected dose plane. A wide field calibration map is then applied to the relative dose for generating an absolute dose at the preselected dose plane location.

One embodiment is herein referred to as EPIDose™ and provides an EPID-to-Dose conversion that allows IMRT QA to remain dose-based. EPIDose™ includes a physics modeling module that accounts for differences such as output factor variation and dose distribution kernels between EPID response and tissue dose. A user may configure a physics model for each linear accelerator (e.g. a Linac) energy level being used. The EPIDose™ physics modeling may incorporate baseline absolute dose measurements from a high resolution dose detector array, by way of example, to create a unique calibration for predicting an absolute dose. This EPIDose™ physics model fuels an EPIDose™ process, which when applied to a raw EPID image in the EPIDose™ process allows the image to be converted to a dose plane within seconds.

For one embodiment of the invention, and to satisfy a need for independent and robust analysis as above described, by opening EPIDose™ files in MapCHECK™ software for analysis, complete autonomy from the delivery system is achieved and a complete suite of analysis options is available. MapCHECK™ is a two dimensional detector array useful in providing a quick and precise verification of radiotherapy dose distributions. While other systems may be used, MapCHECK™ is herein presented by way of one example for use with embodiments of the invention and is a product of Sun Nuclear Corporation of Melbourne, Fla. and includes a two dimensional detector array for a quick and precise verification of radiotherapy dose distributions in addition to analysis software designed specifically for radiation dose QA. Details regarding MapCHECK™ may be found at www-.sunnuclear.com, the disclosure of which is herein incorporated by reference in its entirety.

With regard to EPID based radiation dose QA of the teachings of the present invention, embodiments of the invention, herein referred to as the EPIDose™, provide a solution to any EPID image to dose for a radiation therapy machine from any manufacturer to dose, such as described in U.S. Pat. Nos. 6,888,919 of Varian Medical Systems, Inc. and 6,810,108 of Siemens Medical Solutions USA, Inc.

As above described, the EPIDose™ process may include a first step using raw EPID input. The EPID is projected to a desired dose plane location and corrected for Output Factor differences between EPID and dose. By way of example, a correction may be made for each and every multileaf collimator (MLC) sub-field to correct for "source distribution" of scattered photons and variations in response off axis and under MLC leaves. Further, the results of step one may be convolved with a "Dose Redistribution Kernel" which converts the dose from EPID point spread function (typically sharper than a dose kernel in tissue or tissue-equivalent media) to a tissue equivalent deposition of dose at a modeled QA depth. Relative comparisons with MapCHECK™ array measurements or a treatment planning system (TPS) may be performed, by way of example. Absolute dose comparisons may be performed after the step including an application of a wide-field calibration that may have been pre-stored in the model using MapCHECK™ calibration files.

EPIDose™ includes Physics Modeling that may be configured and optimized (per Linac, energy, delivery mobility) for a specific EPIDose™ setup. By way of example, after EPIDose™ completing initial physics modeling, it is not required again unless the EPID response drifts, is recalibrated or is serviced. Yet further, EPID image acquisition may be done at convenient and multiple EPID detector distances (typically from 100 cm to 140 cm or 145 cm), at any gantry angle, and without the need for buildup material on the imager.

BRIEF DESCRIPTION OF DRAWINGS

For a fuller understanding of the invention, reference is made to the following detailed description, taken in connection with the accompanying drawings illustrating various embodiments of the present invention, in which:

FIG. 11 is a diagrammatical illustration of an EPID image modified to a relative dose through use of a redistribution kernel;

DESCRIPTION OF EMBODIMENTS

The present invention will now be described more fully with reference to the accompanying drawings in which alternate embodiments of the invention are shown and described. It is to be understood that the invention may be embodied in many different forms and should not be construed as limited to the illustrated embodiments set forth herein. Rather, these embodiments are provided so that this disclosure may be thorough and complete, and will convey the scope of the invention to those skilled in the art.

Figure 1:
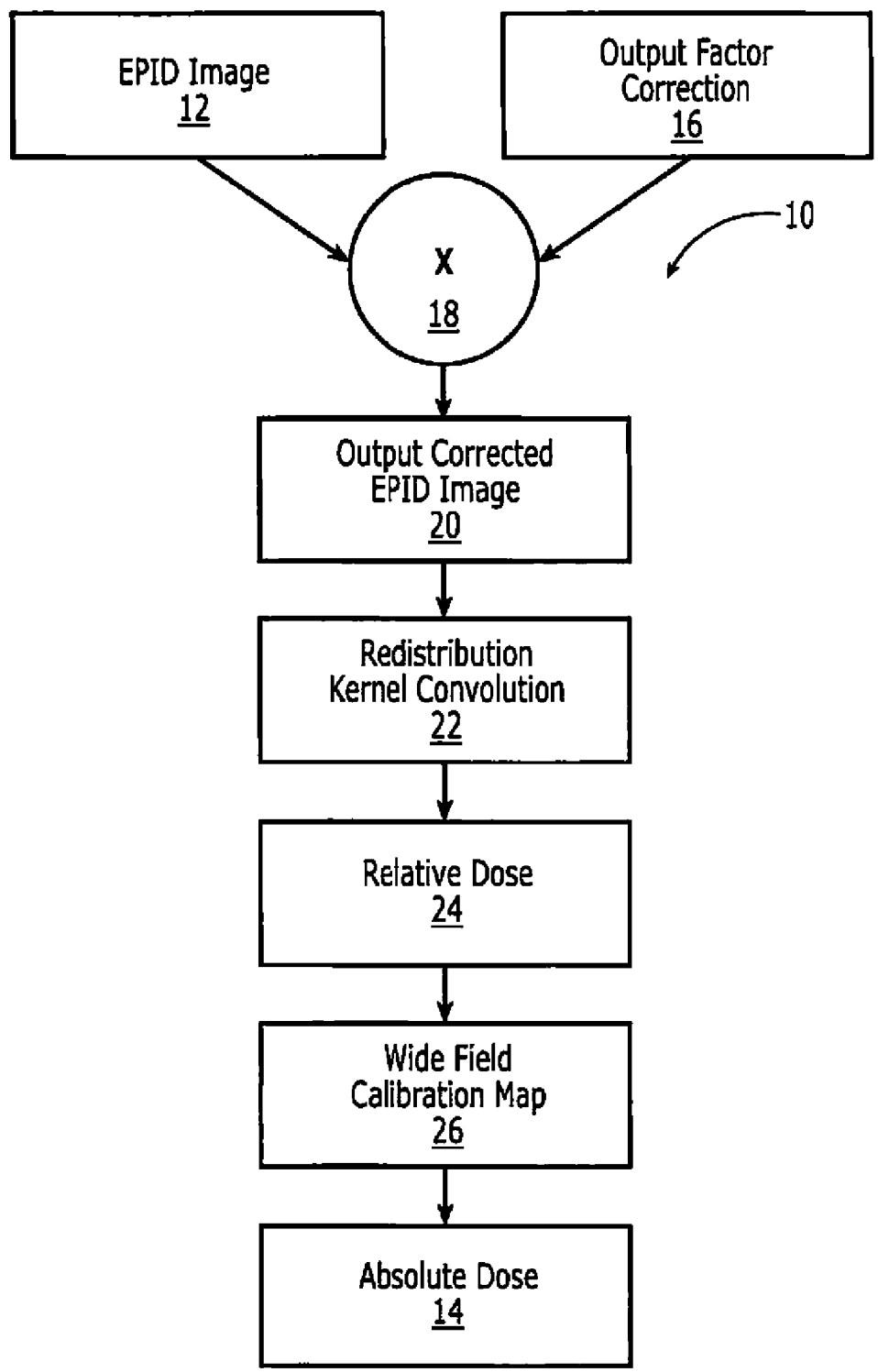
FIG. 1 is a flow chart illustrating one embodiment of an EPID image to Dose conversion process in keeping with the teachings of the present invention.

With reference initially to FIG. 1, a system 10 for converting electronic portal imaging device (EPID) images 12 to an absolute dose 14 comprises means for generating an output factor correction map 16 specific to a radiation treatment beam and means 18 for multiplying the EPID image by the output factor correction map for generating an output corrected EPID image 20. The output corrected EPID image 20 is then convolved with a redistribution kernel 22 for generating a relative dose 20 at a preselected dose plane. A wide field dose calibration map 26 is then applied to the relative dose 24 for generating the absolute dose 14 at the preselected dose plane location. By way of example, multiplying may comprise multiplying each data point including an output value from the EPID by a corresponding spatial data point of the map or kernel.

Figure 3:
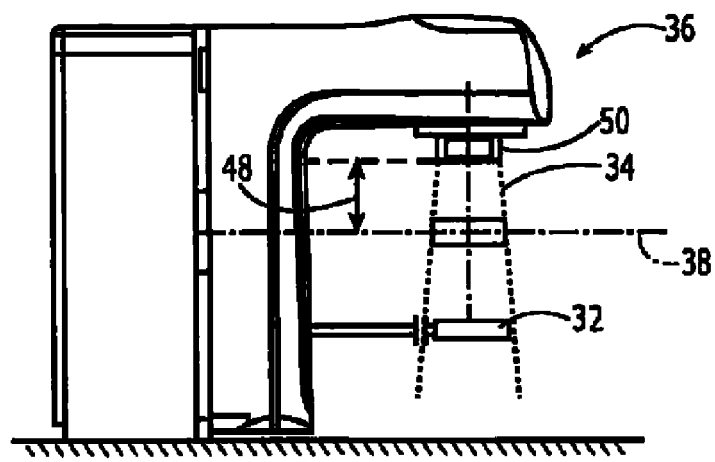
FIG. 3 is a partial side view of illustrating one known radiation treatment system employing an EPID.
Figure 4:
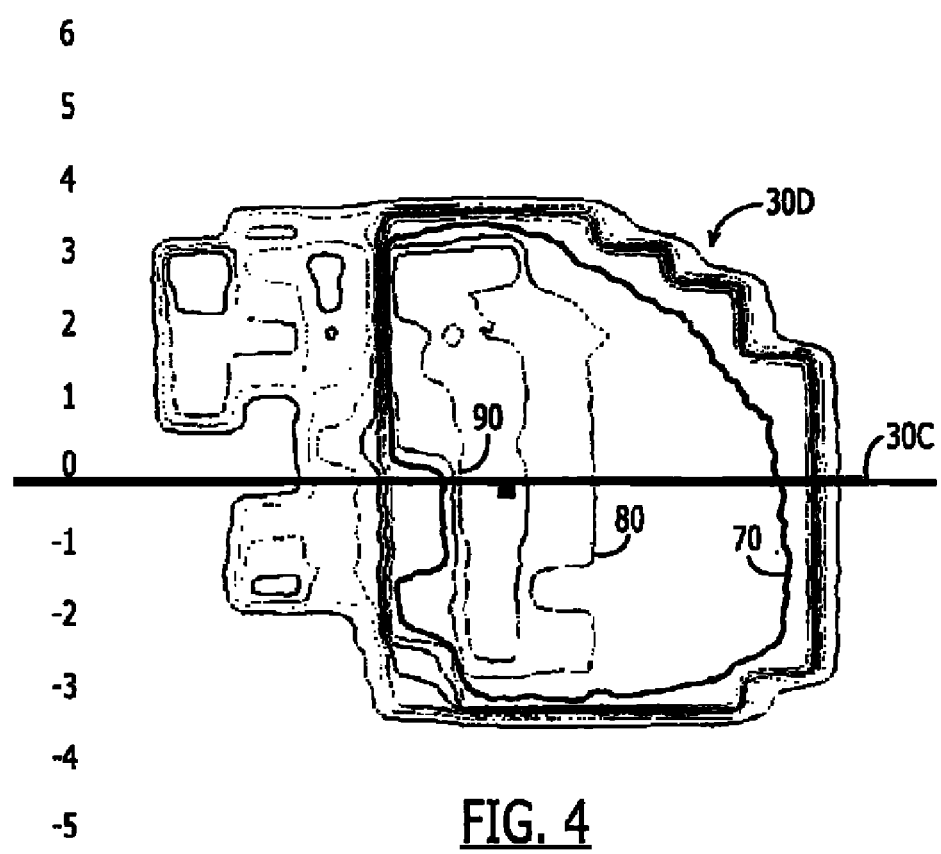
FIG. 4 illustrates one embodiment of a 2-D raw EPID image in a contour map, wherein numerals for each contour are presented in units of relative pixel value compared to a maximum pixel value in percent, by way of example.
Figure 5:
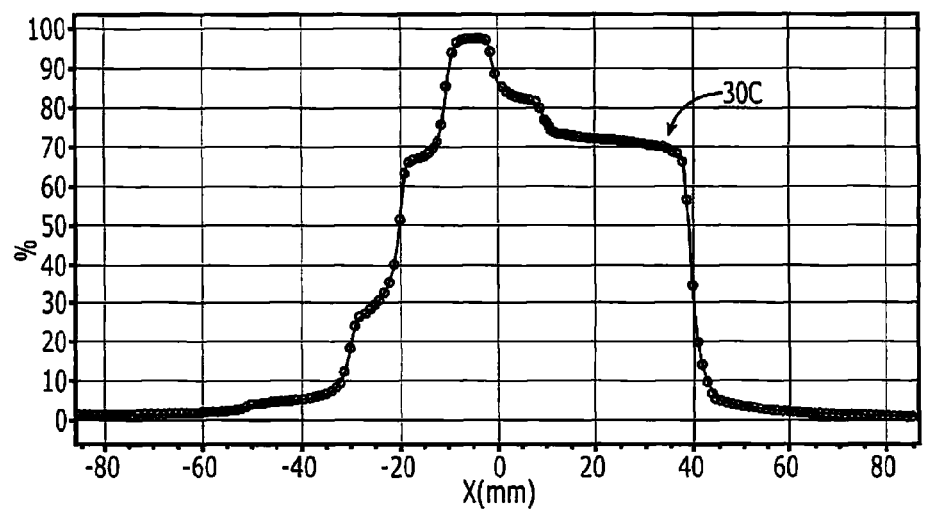
FIG. 5 is a one dimensional profile of the raw EPID image of FIG. 4 taken through a central axis.

The system 10 may be further described with reference to FIG. 2, wherein the EPID image may be selected from a raw EPID image 30 resulting from an EPID 32 positioned within a radiation treatment beam 34 in a radiation treatment apparatus 36, as illustrated with reference to FIG. 3. The raw EPID image 30 may then be geometrically corrected to a preselected dose plane 38, such as a plane including a radiation treatment location, for providing the EPID image 12 as a projected EPID image 40. As is typical in the art, the raw EPID image 30 may be provided by the device 32 as an amorphous silicon panel for receiving the radiation beam 34 and providing a digital image 30D of the raw EPID image 30, as illustrated with reference to FIG. 4 in a 2-D profile and FIG. 5 illustrating a one dimensional profile 30C through a central axis of the digital image 30D.

As above described, an output factor correction map 16 is developed specific to the radiation treatment beam 34. As illustrated with reference to FIG. 6, the projected EPID image 40 is then multiplied by the output factor correction map 16 (i,j pixel X i,j pixel) for generating the output corrected EPID image 20. By way of illustration, one output correction factor map 16 is illustrated with reference to FIG. 7.

Figure 6:
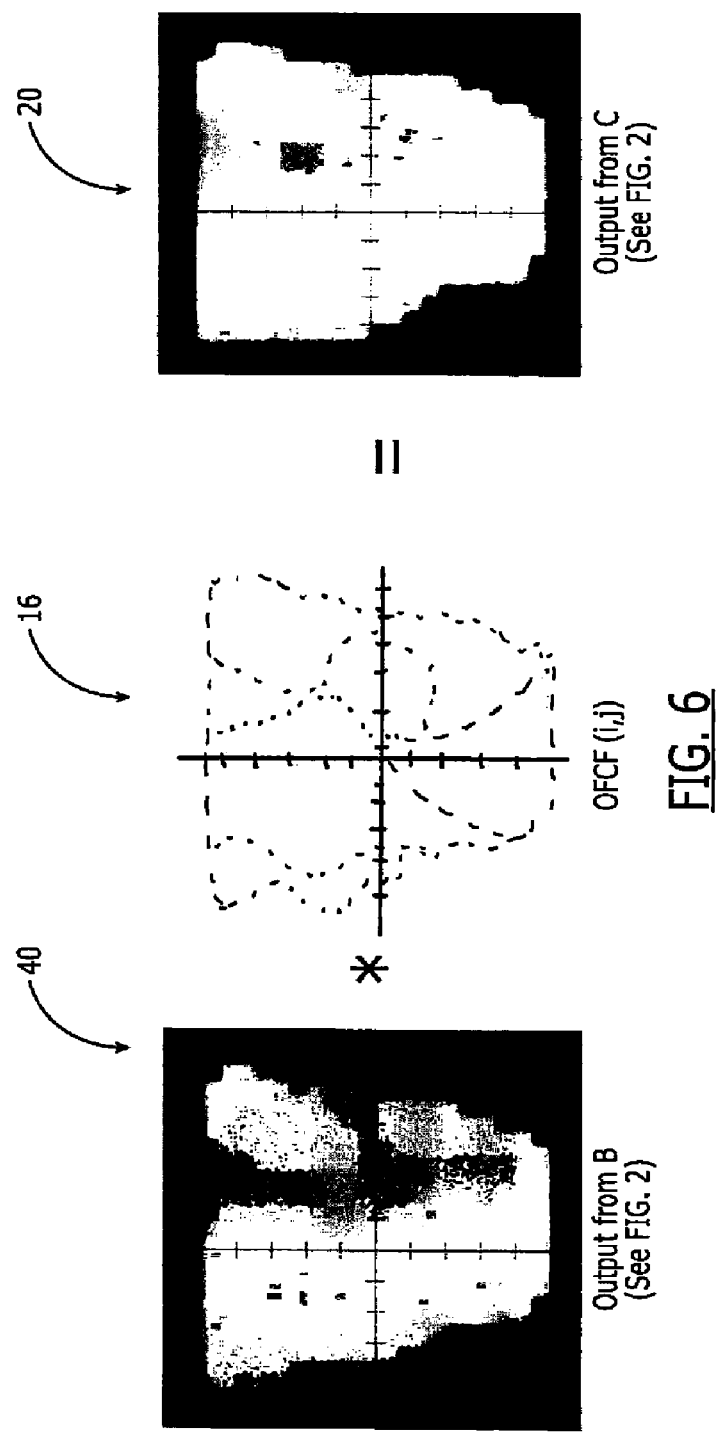
FIG. 6 is a diagrammatical illustration of EPID images and a correction factor for converting one EPID image to another based on operating performance of the radiation treatment apparatus and beam.
Figure 7:
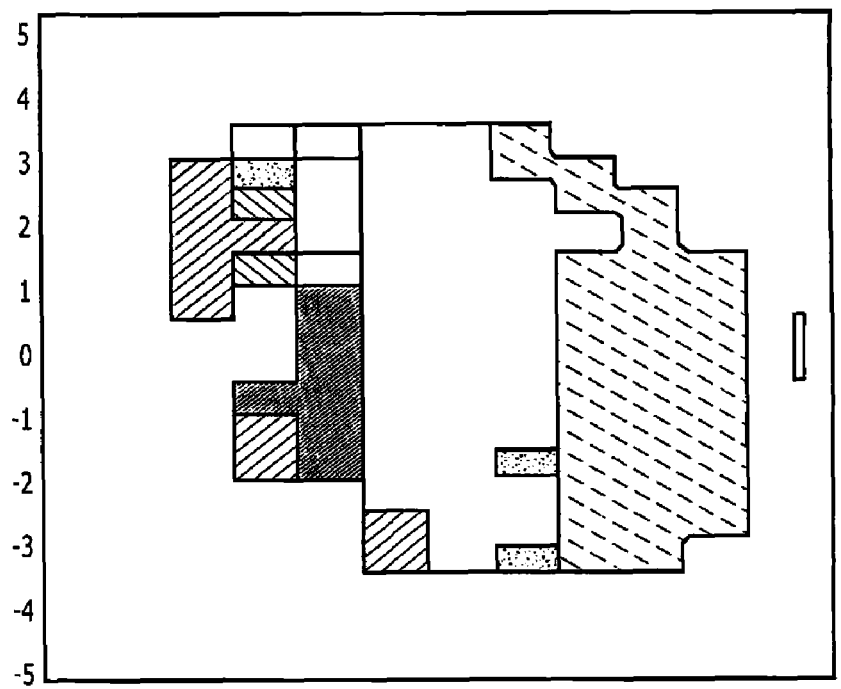
FIG. 7 is a diagrammatical illustration of a digital contour map for one output factor correction map.
Figure 8:
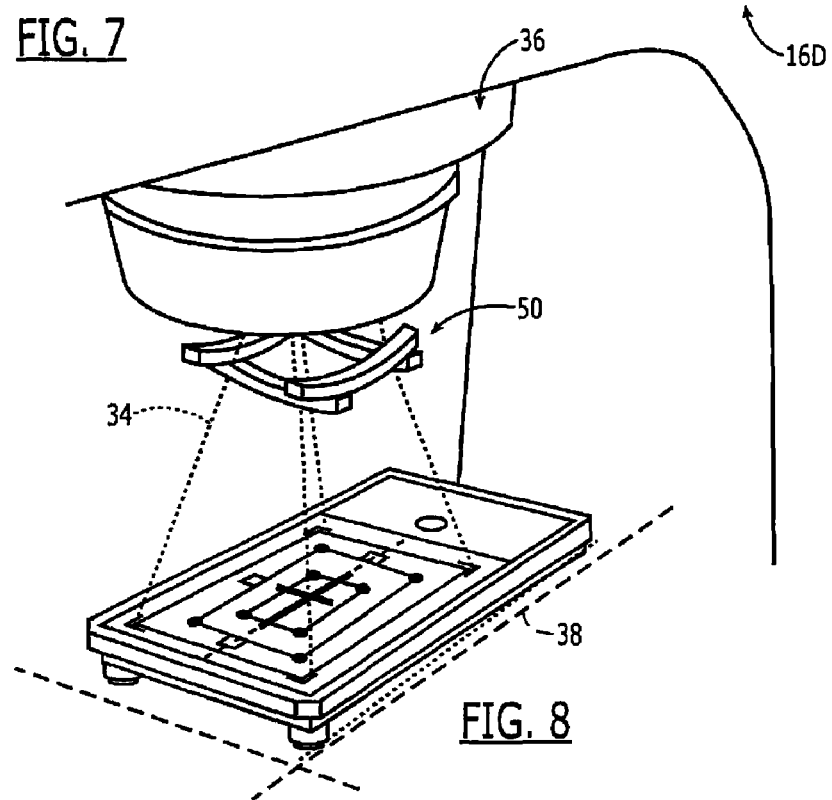
FIG. 8 is a partial perspective view of a radiation treatment apparatus employing a multileaf collimator and a known beam profiler useful with embodiments of the present invention.

By way of further illustration, reference is made to FIG. 6 illustrating a modification of the projected EPID image 40 to the output corrected EPID image 20 using the output factor correction map 16, earlier described with reference to FIG. 1. The 2-D output factor correction map 16 is further illustrated in a digital format as map 16D in FIG. 7 by way of further example. As a result, the projected 2-D EPID image (i,j pixels) multiplied by the 2-D output correction map (corresponding i,j pixels) results in the output corrected 2-D array (i,j). As herein presented by way of example with reference again to FIG. 2, a 2-D output factor correction map specific to an exact beam setup and EPID image is calculated using IMRT beam parameters (segment shapes and weights for every IMRT sub-segment) and the parameters of a physics model. As illustrated with reference again to FIG. 3 and to FIG. 8, after the EPID image has been projected to the preselected dose plane 38 a Source-to-Dose Plane distance 48 (see also FIG. 2, block C), a multileaf collimator (MLC) 50 may typically be employed to provide the intensity modulated radio therapy (IMRT) dose above described.

Figure 9:
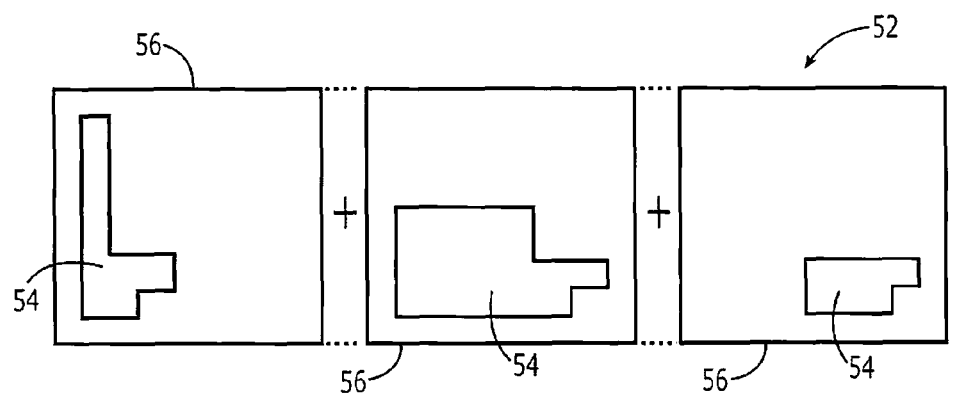
FIG. 9 provides a diagrammatical illustration of a treatment zone and radiation segments used within the EPID image correction process.

With reference to FIG. 9, it is well known in the art that scanning segments of the multileaf collimator 50 to cover a treatment zone 52 such as a tumor, results in highly modulated beam profiles even though individual segments 54 are relatively homogeneous in intensity. For the process herein described, each profile is treated as being defined within an irregular but un-modulated segment 54. The output factor correction map 16 may be derived from the size and shape of a segment field 56 and output factor values for the projected EPID image 40. Steps in the process may comprise identifying a treatment volume or zone 52, identifying a plurality of segments 56 created by a movement of the multileaf collimator (MLC) 50, selecting a field size for each of the plurality of segments, creating an individual output factor correction for each of the plurality of segments, and establishing an overall output correction factor map from a collection of substantially all individual output correction factors.

Figure 10:
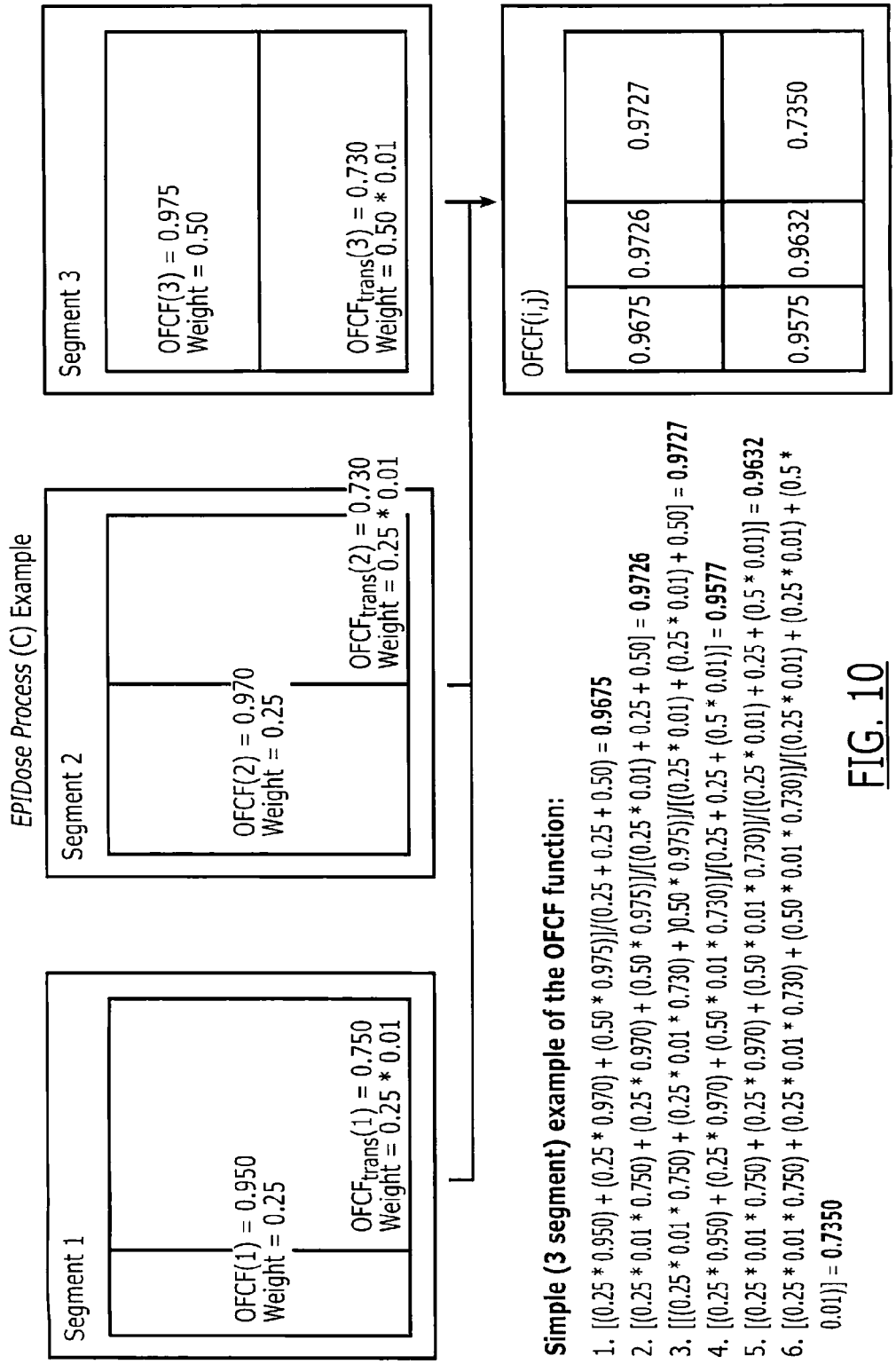
FIG. 10 is a flow chart illustrating a portion of one output correction process in keeping with the teachings of et present invention.

The process may be further described by way of example with reference to the annotated flow chart of FIG. 10 illustrating a three segment example of the correction.

With continued reference to FIG. 6, and by way of example for a computational logic of the output correction map function, consider the following process steps: after the EPID has been projected to the Source-to-Dose Plane distance (see FIG. 2, block C), if a multileaf collimator (MLC) file is chosen, then do the "C" correction. If the MLC file is left blank, prompt a user for a single equivalent field size (this may be used for fields without MLC control points, such as simple un-modulated fields or fields modulated in intensity by solid modulators, such as alloy compensators). For each sub-field "n" in the IMRT beam (N sub fields), create an Output Factor Correction Factor 2-D correction mask/map by setting each exposed pixel to have a value equal to the modeled OFCF (EPID to Dose correction) for that sub-field, and each pixel under the MLC to have a fixed correction value that is diluted by the estimated MLC transmission. This will create a series of OFCFn(i,j) masks/maps for the IMRT field. Compute the overall OFCF(i,j) mask by creating a weighted average of all the OFCF pixels (weighted average for all pixels exposed by more than one sub-field). The weighted average is based on the sub-field weights (n) that expose each pixel normalized to the total exposure weight seen by each pixel. Then, multiple each EPID pixel by its corresponding OFCF pixel, i.e. Output C(i,j)=EPID(i,j)*OFCF(i,j).

Once the output corrected EPID image 20 is obtained as above described by way of example, it is modified by convolution with the redistribution kernel 22, as illustrated with reference to FIG. 11 and earlier with reference to FIG. 1, for generating the relative dose 24 at the preselected dose plane 38, earlier described with reference to FIGS. 1 and 2. The redistribution kernel provides a correction factor for modifying a dose measurement in air to an equivalent dose measurement in water.

One computational logic for obtaining the normalized kernel 22 (a Dose Redistribution Function), may be described by way of example to include the steps of finding a shape of the kernel through an iteration to best fit versus known profiles, then normalizing by rastering through the 2-D (e.g. 10 mm×10 mm) radial scatter kernel K(r) and keeping a running sum of the kernel values, and dividing each kernel element by the area kernel sum to provide a normalized kernel (e.g. area sum=1.00). Call this KNORM(r).

Continue by stepping through all EPID pixels to modify the array value (to derive D from C) as follows: For each pixel (i,j), sum (by "collecting") the scatter dose from surrounding pixels: Do for all C(i,j)>=D threshold, Centered on (i,j), raster through the surrounding 10 mm×10 mm area, and From each surrounding pixel (m,n), "collect" the redistributed dose: Output D(i,j)=KNORM(sqrt[(i−m)2+(j−n)2])*Output C(m, n). Alternatively an FFT convolution may be employed for a faster process than a superposition, specifically by employing a 2-D Fast Fourier Transform (FFT) method.

Figure 12:
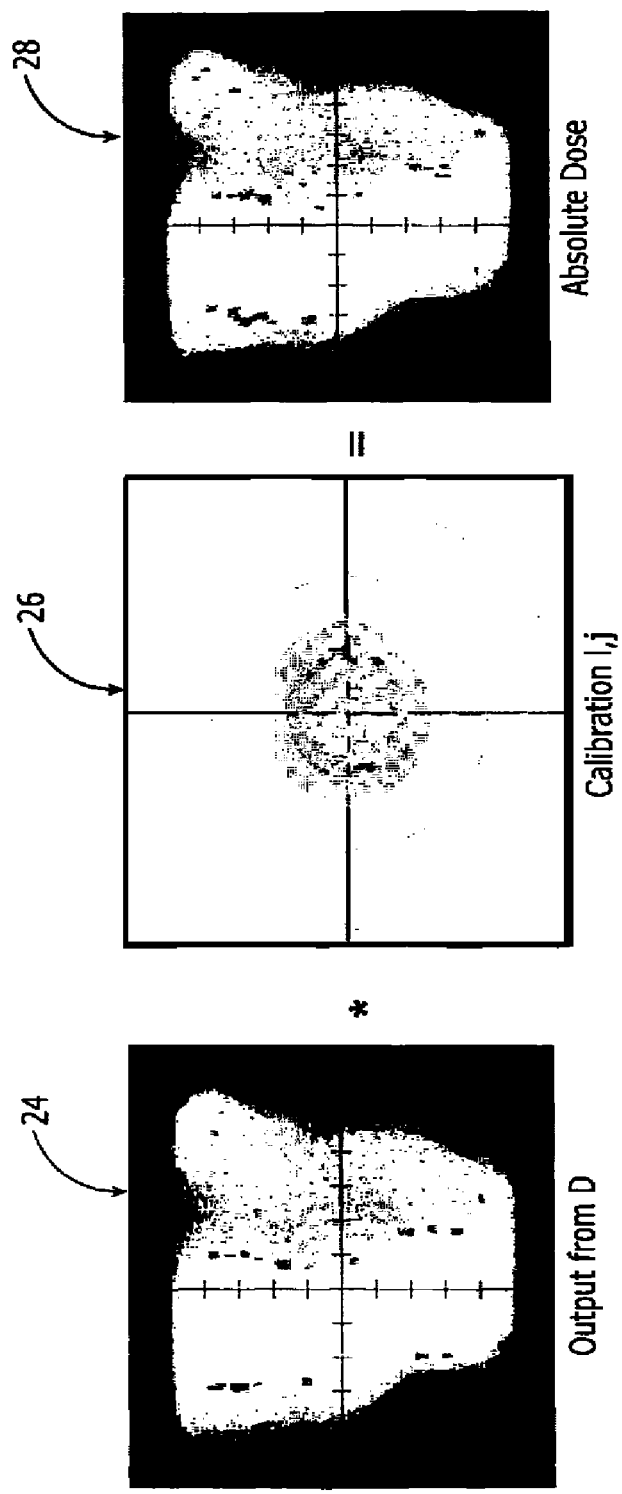
FIG. 12 is a diagrammatical illustration of a relative dose modified to an absolute dose through use of a wide field dose calibration map.
Figure 13:
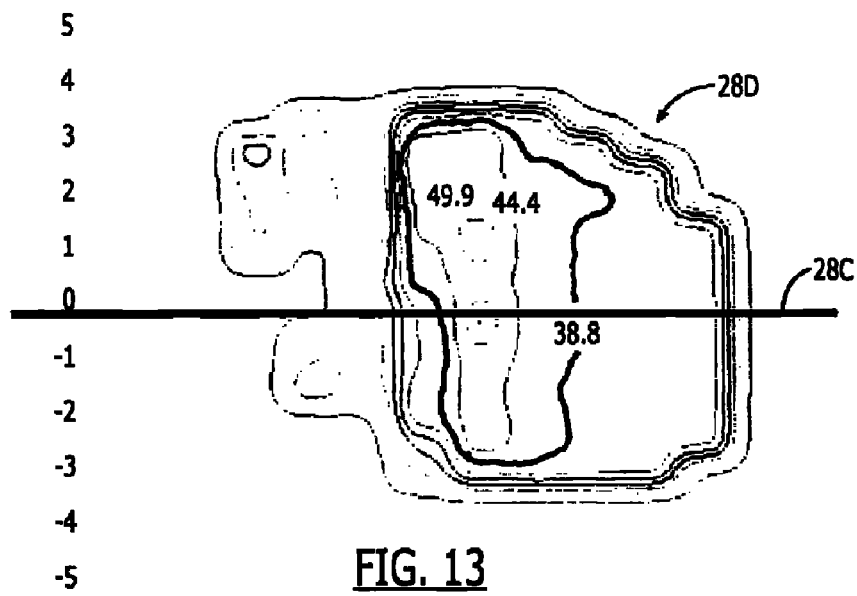
FIG. 13 illustrates one embodiment of a 2-D absolute dose contour map, wherein numerals for each contour are presented in units of cGy, by way of example.
Figure 14:
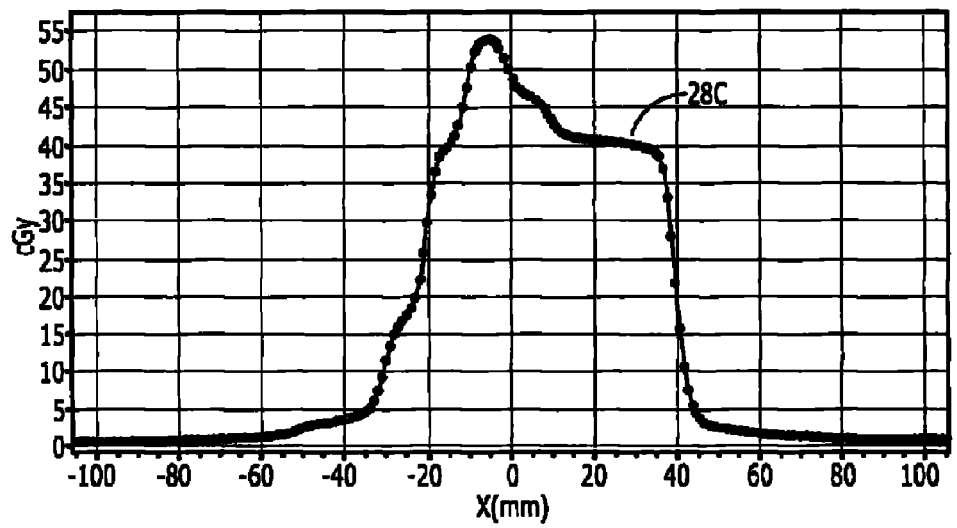
FIG. 14 is a one dimensional profile of the absolute dose of FIG. 13 taken through a central axis.
Figure 15:
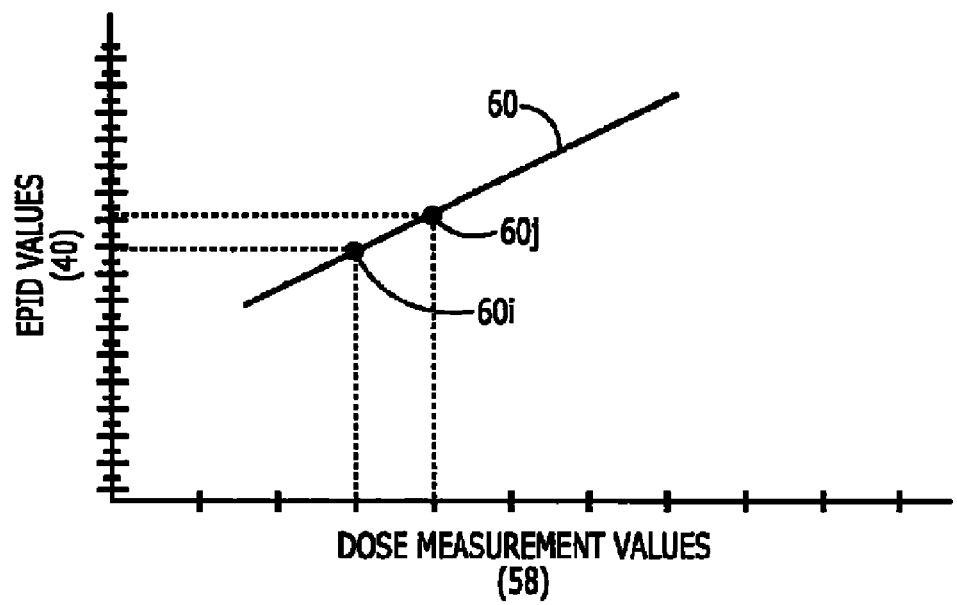
FIG. 15 is a diagrammatical relationship a derived EPID image to measured dose value illustrating construction of an EPID image to Dose Factor for use in generating a wide field dose calibration map used to convert a relative dose to an absolute dose.

With reference again to FIGS. 1 and 2, and now to FIG. 12, providing a physics model or commissioning the EPID (see A-G of FIG. 2, by way of example) includes applying the wide field dose calibration map 26 to the relative dose 24 generates the absolute dose 28 at the preselected dose plane location 38, described earlier with reference to FIGS. 3 and 8. By way of example, and with reference to FIG. 15, generating the wide field dose calibration map 26 comprises comparing derived values for the output D array 40 to measured absolute dose values 58 at a first set of discrete locations within a 2-D plane in the preselected dose plane 38 for providing an output D array-to-dose factor/function 60, and selecting a second set of corresponding discrete locations within the 2-D plane for use in generating the calibration map 26. The output D array-to-dose factor 60 is then applied to each of the discrete locations (pixels) within the second set via a linear calibration equation (slope and intercept, e.g. between adjacent data points 60i and 60j, by way of example) for obtaining the calibration map for all the 2-D locations (pixels) of interest.

With reference again to FIG. 2, embodiments of the invention may comprise commissioning by comparing the estimated planar absolute dose 14 with measured absolute dose 58. The measured absolute dose may be obtained using measurement results from a two dimensional detector array measuring radiotherapy dose distributions, such as available using the MapCHECK™ system earlier described.

Figure 2:
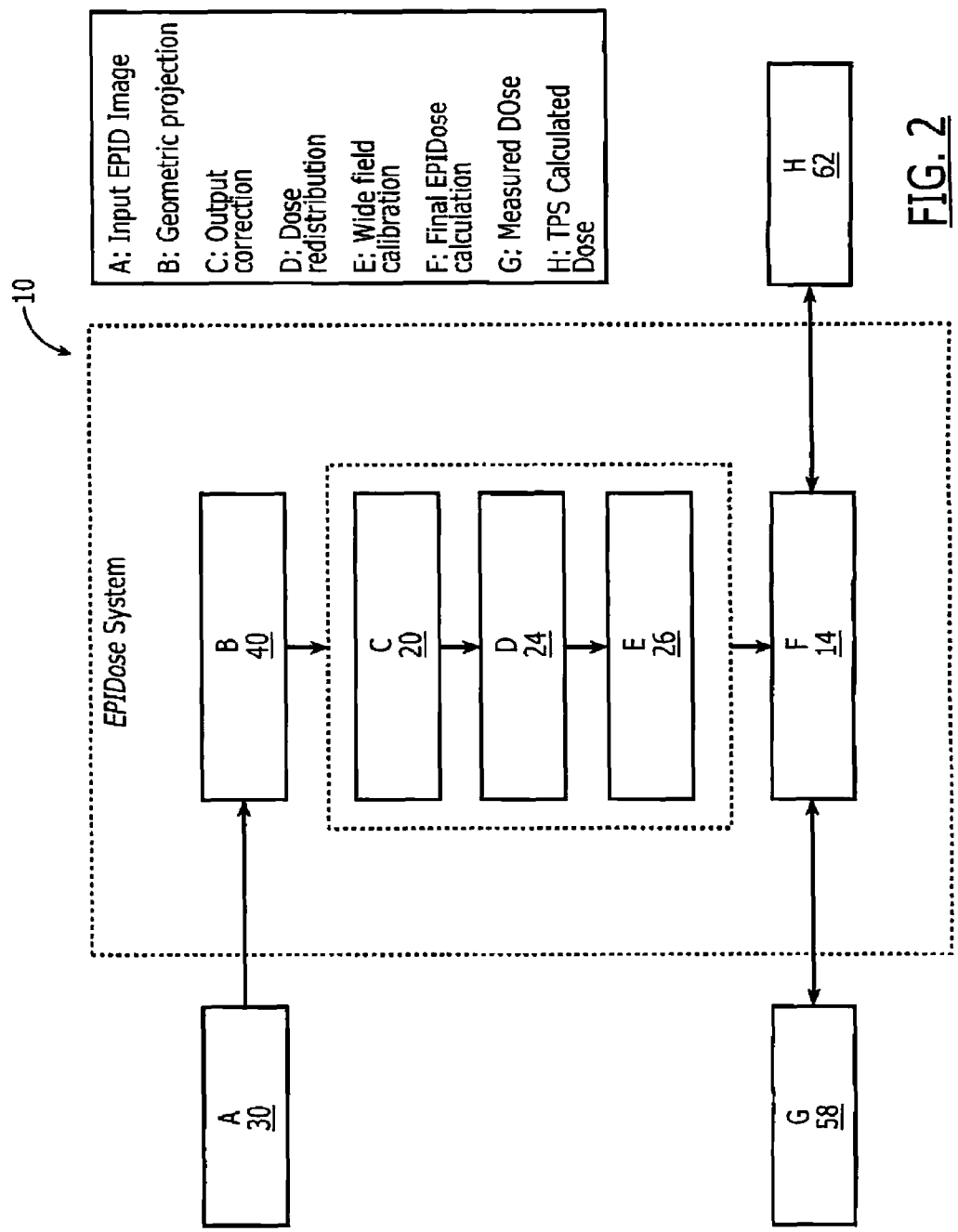
FIG. 2 is a flow chart further illustrating embodiments of the invention including optional steps directed to satisfying needs in radiation therapy treatment.

Yet further, and with continued reference to FIG. 2, the absolute dose 28 may be compared to a dose calculated by a treatment planning system (TPS) 62 for performing dose/IMRT QA for planned fields.

By way of further example, and as described above, a correction may be made for each and every multileaf collimator (MLC) sub-field to correct for a source distribution of scattered photons and variations in response off axis and under MLC leaves. Further, the output corrected EPID may then be convolved with a Dose Redistribution Kernel which converts the dose from EPID point spread function (typically sharper than a dose kernel) to a water equivalent deposition of dose at a modeled QA depth. Relative comparisons using MapCHECK™ array measurements or a treatment planning system (TPS) may be performed. The absolute dose comparisons may include an application of the wide-field calibration that may have been pre-stored in the model using MapCHECK™ calibration files.

Figure 16:
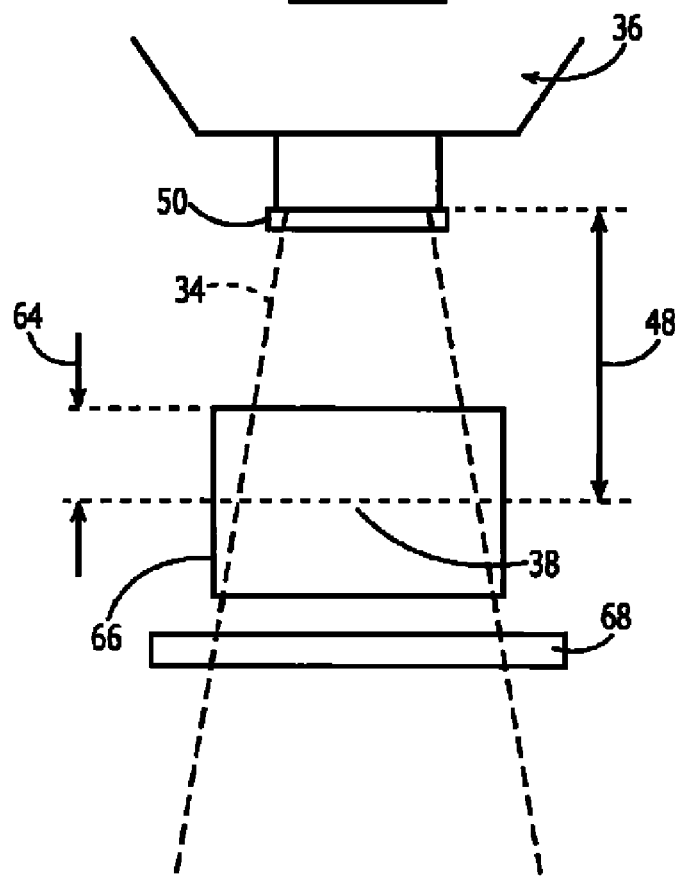
FIG. 16 is a diagrammatical illustration of one radiation treatment dose measurement configuration.

As above described, the redistribution kernel 22 provides a correction factor for modifying a dose measurement in air to an equivalent dose measurement in water. As will be understood by those of ordinary skill in the art, a treatment plan will typically be established with the result that measurements may account for a modeled QA depth 64 in water using a phantom 66 based on the established preselected dose plane or treatment plane 38 and its source to plane distance 48, as illustrated with reference to FIG. 16. The measured dose may use the MapCHECK™ or similar measurement device 68 positioned at various desired locations within the beam 34

To further illustrate embodiments of the invention through commercially available products, one system 10 may comprise a MapCHECK™ EPIDose™ system for an EPID image file via the format DICOM RT (digital imaging and communications in medicine for radiation therapy) Image, selecting an associated plan file (DICOM RT Plan) to gather the MLC segment data, selecting the appropriate EPIDose model, and then converting to a simulated dose plane. This dose plane, derived from a measured EPID image may then be compared to a dose plane generated by the treatment planning system (TPS). The EPIDose™ process provides the measured dose plane. IMRT QA analysis and a commissioning of the EPIDose™ are illustrated with reference to FIGS. 2 and 3. A correlation logic algorithm calculates a two dimensional array of pixel correction values based on inputs from a DICOM RT plan and/or MLC files, by way of example, for providing an output factor correction factor. A dose distribution function is established for modifying array values. A two dimensional wide field calibration map is then established for converting a relative dose to an absolute dose to provide the simulated dose.

By way of further example by assessing the efficacy and quantifying the accuracy of results for embodiments of the present invention, one method is reviewed for IMRT QA in which the measured dose plane is derived from an EPID image, a Si EPID data was acquired and converted using the teachings of the present invention for a method based on a machine-specific beam model to estimate QA dose planes from mega voltage (MV) EPID images. Dose planes were calculated in a homogeneous, water-equivalent QA phantom using the model and an acquired MV EPID image with no additional build-up required on the EPID. Specific parameters, such as field size output dependency, dose redistribution kernel, potential off-axis corrections and absolute dose calibration, were measured to create the model that is based on raw EPID files.

QA dose planes were compared to MapCHECK™ diode array measurements, and also to dose planes calculated by Philips Pinnacle® TPS and the Varian Eclipse TPS. MapCHECK™ measurements and TPS IMRT QA calculations were acquired at a source to detector distance (SDD) of 100 cm at 5 cm water equivalent depth. Corresponding EPIDose dose planes were estimated using EPID images acquired at 140 cm source-to-EPID distance for the attached EPIDose Performance Set 1 and at 105 cm source-to-EPID distance for Sets 2 and 3. Data was collected for both 6 MV (see attached EPIDose Performance Set 1 and Set 2) and 10 MV (see attached Set 3) energies to determine the accuracy of EPIDose for a range of clinical energies. Preliminary analyses demonstrated that the dose planes estimated by the model using EPID images of complex IMRT fields result in >98% pass rate of all point measurements from MapCHECK™, employing a 2% dose or a 2 mm distance to agreement criterion. Setup, acquisition and analysis can be performed in a more time efficient manner than is possible with current methods of IMRT QA for this superior data density.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the claims supported by this disclosure.

That which is claimed is:

1. A method for converting electronic portal imaging device (EPID) images to an absolute dose, the method comprising:
    selecting an EPID image for a preselected dose plane location;
    generating an output factor correction map specific to a radiation treatment beam;
    multiplying the EPID image by the output factor correction map for generating an output corrected EPID image;
    providing a redistribution kernel;
    convolving the output corrected EPID image with the redistribution kernel for generating a relative dose at the preselected dose plane; and
    applying a wide field dose calibration map to the relative dose for generating an absolute dose at the preselected dose plane location.

2. A method according to claim 1, wherein the EPID image selecting comprises:
    selecting a raw EPID image resulting from an EPID positioned within a radiation treatment beam; and
    geometrically correcting the raw EPID image to a preselected dose plane location for providing a projected EPID image.

3. A method according to claim 2, wherein the geometrically correcting of the raw EPID image comprises modifying EPID image data to account for beam divergence based on a source-to-detector distance of the device and a preselected source-to-dose plane location.

4. A method according to claim 1, wherein the EPID image is provided by a device comprising an amorphous silicon detector panel positioned for receiving radiation and providing a digital image.

5. A method according to claim 1, wherein the redistribution kernel comprises a point spread function to transform EPID scatter characteristics to tissue equivalent scatter.

6. A method according to claim 5, wherein the convolving generates a relative dose from the EPID point spread function for a water equivalent deposition of dose at a modeled quality assurance (QA) depth.

7. A method according to claim 1, wherein the output factor correction map generating is derived from segment field size and output factor values for the radiation beam including sub-segments in an intensity modulated radio therapy (IMRT) beam.

8. A method according to claim 1, wherein the output factor correction map generating step comprises:
    identifying a plurality of segments created by a movement of a multileaf collimator (MLC);
    create an individual output factor correction for each of the plurality of segments; and
    establish an overall output correction factor map from a collection of substantially all individual output correction factors.

9. A method according to claim 1, wherein the multiplying of the EPID image by the output factor correction map for generating an output-corrected EPID image comprises multiplying each spatial data point within an EPID image array by a corresponding spatial data point within a correction map array.

10. A method according to claim 1, wherein providing a redistribution kernel comprises providing a correction factor for modifying a radiation measurement by the EPID to an equivalent dose measurement in water.

11. A method according to claim 1, wherein applying a wide field dose calibration map to the relative dose for generating an absolute dose at the preselected dose plane location comprises:
   comparing output-corrected and dose-redistributed two dimensional (2-D) array values to measured absolute dose values at a first set of discrete locations within a 2-D plane in the preselected dose plane for providing an EPID image to dose factor;
   selecting a second set of discrete locations within the 2-D plane for use in the calibration map; and
   applying the EPID image to dose factor for each of the discrete locations within the second set by through slope and offset calculations.

12. A method according to claim 1, wherein the correction map generating step comprises generating a 2-D output factor correction map specific to an exact beam setup and calculating the EPID image using IMRT beam parameters and parameters of an EPID to dose conversion physics model.

13. A method according to claim 1, wherein applying the wide field dose calibration map comprises applying a 2-D measurement array for generating the wide field map using the output-corrected EPID image and measured dose plane for multiple monitor unit exposure settings.

14. A method according to claim 1, further comprising comparing the estimated planar absolute dose with measurement results from a two dimensional detector array measuring radiotherapy dose distributions.

15. A method according to claim 1, further comprising comparing the estimated absolute dose plane with a dose calculated by a treatment planning system (TPS) for performing dose/IMRT QA of planned fields.

16. A method according to claim 1, wherein the output factor correction map generating includes physics modeling configured and optimized for at least one of a Linac, EPID, energy, and delivery mobility for a specific setup.

17. A system for converting electronic portal imaging device (EPID) images to an absolute dose, the system comprising:
   a radiation treatment beam;
   an EPID for providing an EPID image resulting from the radiation treatment beam;
   means for generating an output factor correction map specific to the radiation treatment beam;
   means for multiplying the EPID image by the output factor correction map for generating an output corrected EPID image;
   means for providing a redistribution kernel;
   means for convolving the output corrected EPID image with the redistribution kernel for generating a relative dose at the preselected dose plane; and
   means for providing a wide field dose calibration map for applying to the relative dose for generating an absolute dose at a preselected dose plane location.

18. A system according to claim 17, wherein the EPID comprises an amorphous silicon panel positioned for receiving radiation and providing a digital image.

19. A system according to claim 17, wherein the output factor correction map means comprises:
   means for identifying a treatment volume;
   means for identifying a plurality of segments created by a movement of a multileaf collimator (MLC);
   means for selecting a field size for each of the plurality of segments and creating an individual output factor correction for each of the plurality of segments; and
   means for establishing an overall output correction factor map from a collection of substantially all individual output correction factors.

20. A system according to claim 17, wherein the multiplying means comprises means for multiplying each spatial data point within an EPID image array by a corresponding spatial data point within a correction map array.

21. A system according to claim 17, wherein the redistribution kernel means comprises dose measurement means for measuring a dose response from the EPID and an equivalent dose measurement in a tissue-equivalent media.

22. A system according to claim 17, wherein the correction map generating means comprises means for generating a 2-D output factor correction map specific to an exact beam setup and means for calculating the EPID image using IMRT beam parameters and parameters of an EPIDose physics model.

23. A system according to claim 17, further comprising a LINAC for providing the radiation treatment beam.

* * * * *